US012564605B2

(12) United States Patent
El-Khodor et al.

(10) Patent No.: US 12,564,605 B2
(45) Date of Patent: Mar. 3, 2026

(54) PLANT BASED COMPOSITIONS AND METHODS FOR THE DELIVERY OF MAGNESIUM

(71) Applicant: Standard Process, Inc., Palmyra, WI (US)

(72) Inventors: Bassem F. El-Khodor, Palymra, WI (US); John Troup, Palymra, WI (US); Brandon Metzger, Palmyra, WI (US)

(73) Assignee: Standard Process, Inc., Palmyra, WI (US)

( * ) Notice: Subject to any disclaimer, the term of this patent is extended or adjusted under 35 U.S.C. 154(b) by 0 days.

(21) Appl. No.: 16/539,391

(22) Filed: Aug. 13, 2019

(65) Prior Publication Data

US 2020/0046761 A1 Feb. 13, 2020

Related U.S. Application Data

(60) Provisional application No. 62/718,127, filed on Aug. 13, 2018.

(51) Int. Cl.
| | |
|---|---|
| *A61K 33/06* | (2006.01) |
| *A61K 36/21* | (2006.01) |
| *A61K 36/288* | (2006.01) |
| *A61K 36/31* | (2006.01) |
| *A61K 36/36* | (2006.01) |

(Continued)

(52) U.S. Cl.
CPC .............. *A61K 33/06* (2013.01); *A61K 36/21* (2013.01); *A61K 36/288* (2013.01); *A61K 36/31* (2013.01); *A61K 36/36* (2013.01); *A61K 36/42* (2013.01); *A61K 36/48* (2013.01); *A61K*

*36/537* (2013.01); *A61K 36/60* (2013.01); *A61K 36/70* (2013.01); *A61K 36/899* (2013.01)

(58) Field of Classification Search
CPC combination set(s) only.
See application file for complete search history.

(56) References Cited

U.S. PATENT DOCUMENTS

| | | | |
|---|---|---|---|
| 6,558,691 B1 | 5/2003 | Koumarianos | |
| 7,867,525 B2 * | 1/2011 | Bok .......................... | A23F 3/34 |
| | | | 424/728 |

(Continued)

FOREIGN PATENT DOCUMENTS

| | | | | | |
|---|---|---|---|---|---|
| CN | 102302151 A | * | 1/2012 | ............. | A23L 33/00 |
| CN | 104026450 A | * | 9/2014 | ............. | A23L 33/00 |

(Continued)

OTHER PUBLICATIONS

Trifunovic et al. Free radicals and antioxidants: Antioxidative and other properties of swiss chard (*Beta vulgaris* L. subsp. *cicla*). Agriculture & Forestry, vol. 61, Issue 2:73-92. (Year: 2015).*

(Continued)

*Primary Examiner* — Lakshmi S Channavajjala
(74) *Attorney, Agent, or Firm* — Husch Blackwell LLP

(57) ABSTRACT

The disclosure relates to compositions and methods for delivery of magnesium. In one embodiment, the disclosure relates to a composition comprising a first plant based source of magnesium and a second plant based source of magnesium. In on embodiment, the disclosure relates to methods for delivering magnesium to the central nervous system of an individual.

3 Claims, 7 Drawing Sheets

(51) Int. Cl.

| | | |
|---|---|---|
| *A61K 36/42* | (2006.01) | |
| *A61K 36/48* | (2006.01) | |
| *A61K 36/537* | (2006.01) | |
| *A61K 36/60* | (2006.01) | |
| *A61K 36/70* | (2006.01) | |
| *A61K 36/899* | (2006.01) | |

(56) References Cited

U.S. PATENT DOCUMENTS

| | | |
|---|---|---|
| 2009/0264289 A1 | 10/2009 | Dietz et al. |
| 2014/0234488 A1 | 8/2014 | Chang |
| 2015/0064285 A1 | 3/2015 | Liu et al. |
| 2015/0223498 A1 | 8/2015 | Gu et al. |
| 2016/0165941 A1 | 6/2016 | Hofmekler |

FOREIGN PATENT DOCUMENTS

| | | | | |
|---|---|---|---|---|
| CN | 103749997 B | 1/2016 | | |
| WO | 2004016092 A1 | 2/2004 | | |
| WO | WO-2008002175 | * 1/2008 | ............. | A23L 33/40 |

OTHER PUBLICATIONS

Sun et al. Antioxidant activities of buckwheat extracts. Food Chemistry, 90, 743-749, 2005. (Year: 2005).*

Pyo et al. Antioxidant activity and phenolic compounds of Swiss chard (*Beta vulgaris* subspecies *cycla*) extracts. Food Chemistry, 85, 19-26 (Year: 2004).*

Jacob et al. Evaluation of antioxidant and antimicrobial activities of the selected green leafy vegetables. International Journal of PharmTech Research, Jan.-Mar. 2011, vol. 3:1, 148-152 (Year: 2011).*

Jan et al. Physico-chemical, textural, sensory and antioxidant characteristics of gluten e Free cookies made from raw and germinated Chenopodium (*Chenopodium album*) flour. LWT—Food Science and Technology, 71:281-287 (Year: 2016).*

Kushwaha et al., Effect of supplementation of drumstick (*Moringa oleifera*) and amaranth (*Amaranthus tricolor*) leaves powder on antioxidant profile and oxidative status among postmenopausal women. J. Food Science Technology (Nov. 2014)51(11):3464-3469. (Year: 2014).*

International Search Report and Written Opinion for International Application No. PCT/US19/46349 dated Nov. 18, 2019, 8 pages.

Christianson. HuffPost. Are you Eating Buckwheat. Jul. 9, 2015. (Retrieved Sep. 30, 2019) Retrieved from Internet URL: <https://www.huffpost.com/entry/buckwheat_b_7754674>.

Wikipedia. Siraitia grosvenorii. Dec. 16, 2017. (Retrieved Sep. 30, 2019) Retrieved from Internet URL: <https://en.wikipedia.org/wiki/Siraitia_grosvenorii>.

Wikipedia. List of Leaf Vegetables. May 24, 2018. (Retrieved Oct. 30, 2019) Retrieved from Internet: https://en.wikipedia.org/w/index.php?title=List_of_leaf_vegetables&oldid=842817020.

Stanciu et al. Phenolic and Mineral Composition of Wild Chicory Grown in Romania. 2019 (Retrieved Oct. 30, 2019) Retrieved from Internet URL:<https://www.revistadechimie.ro/pdf/14%20STANCIU%204%2019.pdf>.

El-Khodor et al., "Elevation of brain magnesium with Swiss chard and buckwheat extracts in an animal model of reduced magnesium dietary intake", (2022) Nutritional Neuroscience, 25:12, 2638-2649, DOI: 10.1080/1028415X.2021.1995119, 13 pages.

* cited by examiner

PLANT BASED COMPOSITIONS AND METHODS FOR THE DELIVERY OF MAGNESIUM

CROSS-REFERENCE TO RELATED APPLICATIONS

This application claims priority to and is a non-provisional patent application of U.S. Provisional Patent Application No. 62/718,127 filed Aug. 13, 2018, which is incorporated herein by reference in its entirety.

FIELD

The disclosure relates to a plant based composition. In one embodiment, the disclosure relates to a plant based composition with multiple sources of magnesium and methods of administering said composition. In another embodiment, the disclosure relates to methods of increasing magnesium in the cerebrospinal fluid of an individual.

BACKGROUND

Magnesium is the fourth most common cation in our body, the second most common intracellular cation and the most common intracellular divalent cation. The human body contains around 25 grams of magnesium. Magnesium is a cofactor in more than 300 enzyme systems that regulate diverse biochemical reactions in the body, including protein synthesis, muscle and nerve function, blood glucose control, and blood pressure regulation. Magnesium is required for energy production, oxidative phosphorylation, and glycolysis. It contributes to the structural development of bone and is required for the synthesis of DNA, RNA, and the antioxidant glutathione. Magnesium also plays a role in the active transport of calcium and potassium ions across cell membranes, a process that is important to nerve impulse conduction, muscle contraction, and normal heart rhythm.

Because magnesium has so many critical functions, the body has mechanisms to assure that it is readily available to perform them. During low intakes of magnesium, the percent absorbed from the diet is increased, the amount in urine is decreased, and body reserves (bone is the major reserve) are used. When dietary intake of magnesium is adequate, the opposite occurs. Thus, the response of the body to maintain magnesium homeostasis when changes in dietary intakes occur has made it difficult to establish indicators of magnesium deficiency. Dietary intake and serum concentration of magnesium are used typically as markers of magnesium status.

Table I lists the current Recommended Daily Allowances for magnesium. For infants from birth to 12 months, the Food and Nutrition Board (FNB) at the Institute of Medicine of the National Academies established an Adequate Intake for magnesium that is equivalent to the mean intake of magnesium in healthy, breastfed infants, with added solid foods for ages 7-12 months.

TABLE I

Recommended Dietary Allowances (RDAs) for Magnesium

| Age | Male | Female | Pregnancy | Lactation |
|---|---|---|---|---|
| Birth to 6 months | 30 mg* | 30 mg* | | |
| 7-12 months | 75 mg* | 75 mg* | | |
| 1-3 years | 80 mg | 80 mg | | |
| 4-8 years | 130 mg | 130 mg | | |

TABLE I-continued

Recommended Dietary Allowances (RDAs) for Magnesium

| Age | Male | Female | Pregnancy | Lactation |
|---|---|---|---|---|
| 9-13 years | 240 mg | 240 mg | | |
| 14-18 years | 410 mg | 360 mg | 400 mg | 360 mg |
| 19-30 years | 400 mg | 310 mg | 350 mg | 310 mg |
| 31-50 years | 420 mg | 320 mg | 360 mg | 320 mg |
| 51+ years | 420 mg | 320 mg | | |

*Adequate Intake (AI)

Dietary surveys of people in the United States consistently show that intakes of magnesium are lower than recommended amounts. While no current data on magnesium status in the United States is available, an analysis of data from the National Health and Nutrition Examination Survey (NHANES) of 2005-2006 found that a majority of Americans of all ages ingest less magnesium from food than their respective Estimated Average Requirements (EARs); adult men aged 71 years and older and adolescent females are most likely to have low intakes.

Magnesium deficiency has been associated with increased risk of cardiovascular disease, osteoporosis, and metabolic disorders, including hypertension and type 2 diabetes mellitus. Preliminary studies have shown that magnesium improved insulin sensitivity in individuals at risk for diabetes. Randomized controlled trials have also investigated the role of magnesium supplementation in the prevention of complications following stroke or heart surgery.

Magnesium supplements have tried to address the deficiencies, but absorption of magnesium from different kinds of magnesium supplements varies. However, the body typically absorbs only 20-50% of ingested magnesium. Thus, a need still exits for methods and compositions that can improve magnesium absorption and magnesium delivery.

SUMMARY

In one embodiment, the disclosure relates to compositions and methods for delivery of magnesium. In one embodiment, the disclosure relates to compositions and methods for improved absorption of magnesium. In another embodiment, the disclosure relates to compositions and methods for increasing magnesium in the cerebrospinal fluid of an individual. In another embodiment, the disclosure relates to compositions and methods for increasing free ionic magnesium in the central nervous system of an individual.

In one embodiment, the disclosure relates to a composition comprising a first plant based source of magnesium and a second plant based source of magnesium. In one embodiment, the first plant based source of magnesium is a pseudograin.

In one embodiment, the disclosure relates to a composition comprising a first plant based source of magnesium and a second plant based source of magnesium, wherein the second plant based source of magnesium is a leafy vegetable.

In one embodiment, the disclosure relates to a composition comprising a first plant based source of magnesium and a second plant based source of magnesium, wherein the first plant based source is a pseudograin and the second plant based source of magnesium is a leafy vegetable.

In one embodiment, the disclosure relates to a composition comprising a first plant based source of magnesium and a second plant based source of magnesium, wherein the first plant based source is a pseudograin and the second plant based source of magnesium is a leafy vegetable, and the leafy vegetable is about 50% more on a dry weight basis as compared to the weight of the pseudograin.

In one embodiment, the disclosure relates to a composition comprising a pseudograin and a leafy vegetable, wherein the leafy vegetable and the pseudograin are present at a ratio of 3:2 on a dry weight basis.

In one embodiment, the pseudograin is Buckwheat. In another embodiment, the leafy vegetable is Swiss Chard.

In one embodiment, the disclosure relates to methods for the delivery of magnesium comprising administering a composition as disclosed herein in an effective amount to an individual.

In one embodiment, the disclosure relates to methods for increasing magnesium in the cerebrospinal fluid of an individual comprising administering a composition as disclosed herein in an effective amount to the individual.

In one embodiment, the disclosure relates to a composition that provides plant-based magnesium to bridge dietary gap for this essential mineral.

In one embodiment, the disclosure relates to a composition for the use and support of a naturally occurring Mg for the management of stress and anxiety.

In one embodiment, the disclosure relates to compositions and methods to increases free ionic Mg in the Cerebrospinal fluid (CSF).

In another embodiment, the disclosure relates to compositions and methods to support brain function and cognition In one embodiment, the disclosure relates to compositions and methods comprising plant-based multiform magnesium, delivering Mg in a matrix of whole food components including protein matrix and base.

In one embodiment, the disclosure relates to compositions and methods comprising natural plant based sources of Mg from a ratio of 3:2 from Swiss Chard and Buckwheat.

In one embodiment, the disclosure relates to compositions and methods that deliver a unique blended ratio of Mg and vitamin K.

In one embodiment, the disclosure relates to compositions and methods that contain about 90 mg of Mg, which has 3× greater bioavailability as compared to the salt form of Mg.

In one embodiment, the disclosure relates to compositions and methods having all natural source of plant Mg for support of dietary needs of Mg and meeting or exceeding the daily recommended amounts.

In one embodiment, the disclosure relates to compositions and methods having a blended natural plant source of Mg shown to appear in cerebrospinal fluid (CSF) as compared to synthetic salt forms that are not present in the CSF.

In one embodiment, the disclosure relates to compositions and methods that provide for the delivery and use of plant based Mg, which improves whole body and urine alkalization.

In one embodiment, the disclosure relates to compositions and methods that provide a good source of plant-based Magnesium and vitamin K1.

In one embodiment, the disclosure relates to compositions and methods that provide a good source of vitamin K1 (40 mcg per serving).

Mg) and Diet 5008 (0.20% Mg). The p-value presented is *$p < 0.05$. Data are presented as mean±SEM.

Figure 3:
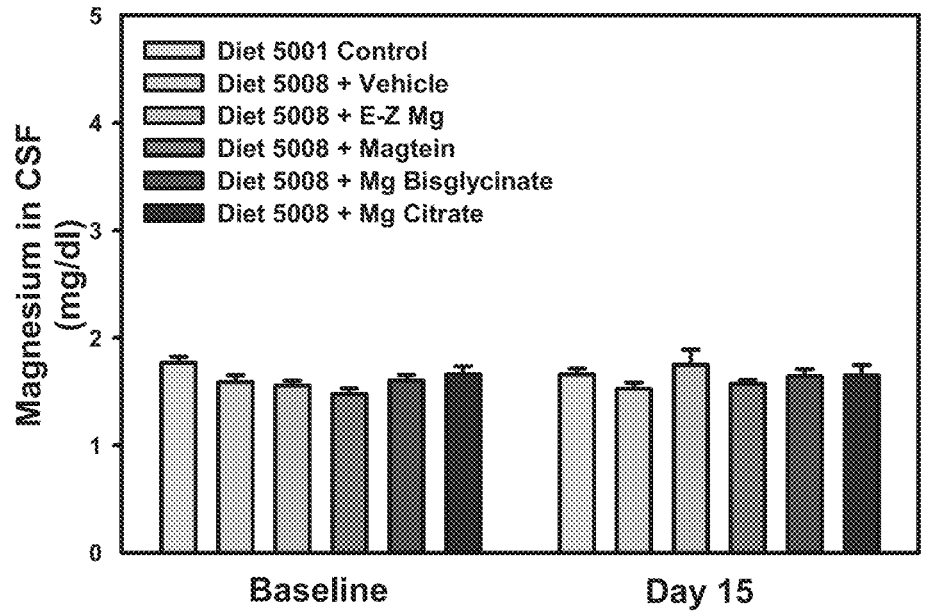

FIG. 3 is a bar graph depicting magnesium in cerebrospinal fluid of animals at a baseline and following 15 days of treatment with various compositions. Data are presented as mean±SEM.

Figure 4:
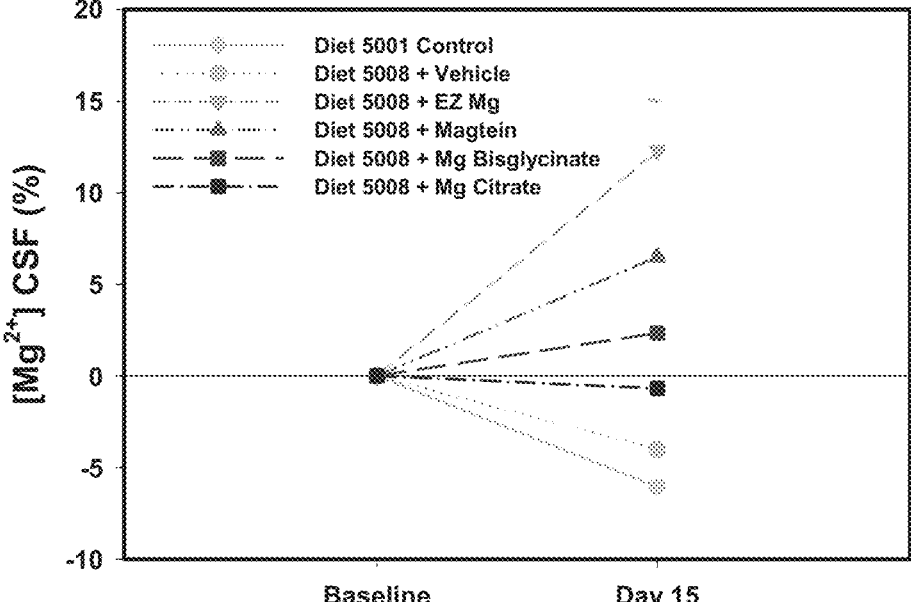

FIG. 4 is a line graph depicting average percent change in CSF magnesium levels. The ~$p < 0.05$ is compared to Diet 5008 plus vehicle treated animals. Data are presented as mean±SEM.

Figure 5:
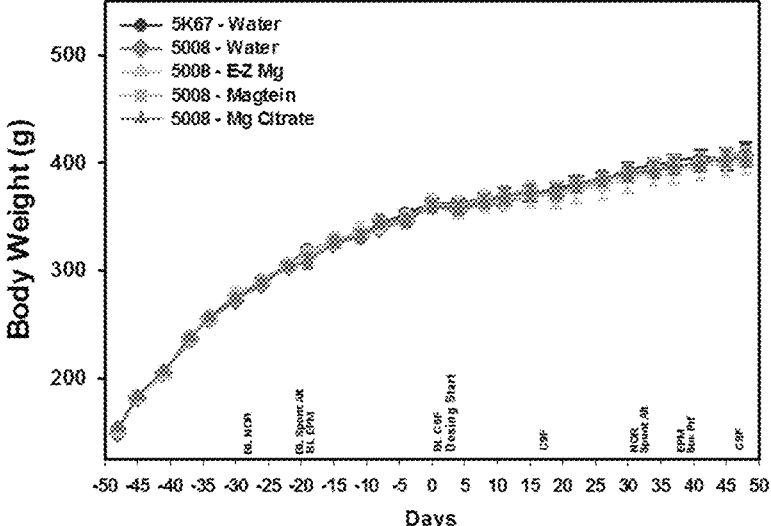

FIG. 5 is a line graph plotting body weights of animals during the study. Data are presented as mean±SEM.

Figure 6:
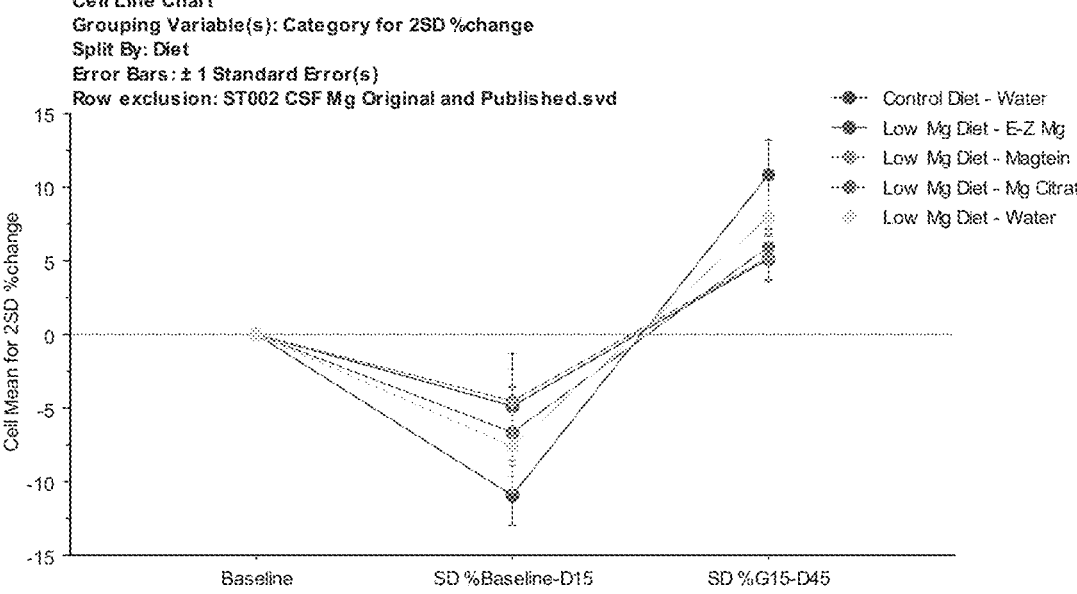

FIG. 6 is a line graph depicting the percent change in CSF free ionic Mg in rats fed low Mg diet and supplemented with various Mg forms.

Figure 7:
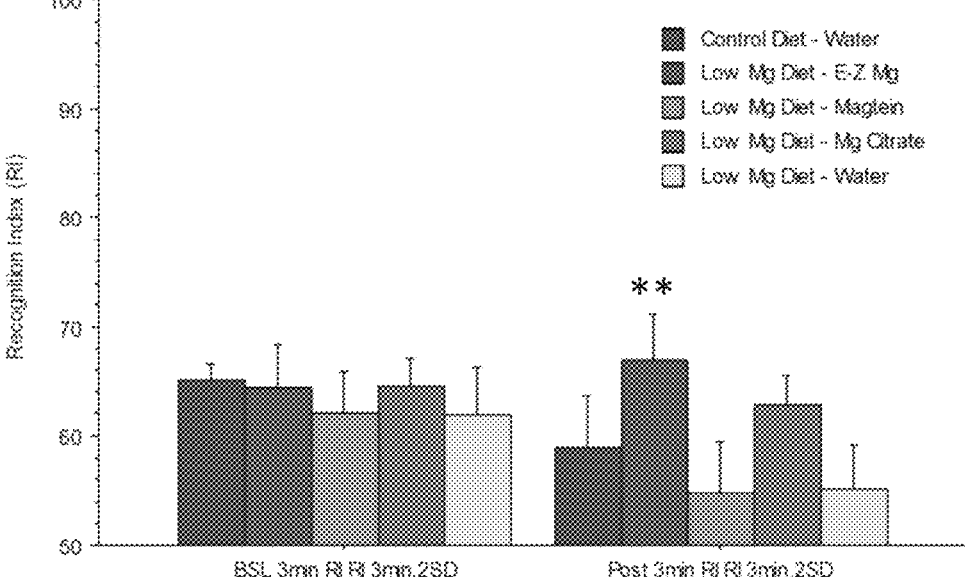

FIG. 7 is a bar graph depicting results of a Novel Object Recognition test where rats fed low Mg diet but supplemented with a composition having two plant-based sources of magnesium (buckwheat and swiss chard) showed improved learning and memory in comparison to rats fed low diet and supplemented with Magtein or placebo.

DETAILED DESCRIPTION

The compositions and methods disclosed herein will now be described more fully hereinafter with reference to the accompanying figures, in which embodiments of the disclosure are shown. The compositions and methods disclosed herein may, however, be embodied in many different forms and should not be construed as limited to the embodiments set forth herein. Rather, these embodiments are provided so that the disclosure will be thorough and complete and will fully convey the scope of the invention to those skilled in the art.

As used herein, the term "and/or" includes any and all combinations of one or more of the associated listed items.

It will be understood that, although the terms first, second, etc. may be used herein to describe various elements, components, regions, and/or sections, these elements, components, regions, and/or sections should not be limited by these terms. These terms are only used to distinguish one element, component, region, or section from another element, component, region, or section. Thus, a first element, component, region, or section discussed below could be termed a second element, component, region, or section without departing from the disclosure.

All patents, patent applications, and non-patent literature references are incorporated herein in their entireties.

I. Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "baseline" refers to an initial level or starting point. In one embodiment, the baseline of a compound can be used to measure effectiveness of a treatment or composition in altering the compound.

As used herein, the term "bioavailability" is referred to as the extent and rate to which the active ingredient or active moiety from a drug product or composition is absorbed and becomes available at the site of action. The relative bioavailability in terms of the rate and extent of absorption is considered predictive of clinical outcomes.

As used herein, "bran" refers to outer layer of cereal grains comprising the aleurone and pericarp.

As used herein, "buckwheat" refers to seed and/or plant parts harvested from *Fagopyrum cymosum*, or *Fagopyrum esculentum*, which is also known as common buckwheat, Japanese buckwheat and silverhull buckwheat, or *Fagopyrum tataricum*, a domesticated food plant common in Asia, but not as common in Europe or North America, or a combination of one or more species.

As used herein, "de-hulled" refers to a seed which has had its hard protective outer covering of a seed, i.e., the seed coat, removed.

As used herein, "effective amount" refers to the administration of an amount of a given compound that achieves a desired effect.

As used herein, "groats" are the hulled and crushed seeds of buckwheat.

As used herein, "hull" refers to hard protective outer covering of a seed, i.e., the seed coat.

As used herein, the term, "isolated" requires that the material be removed from its original environment.

As used herein, the term "placebo" refers to a substance used in controlled experiments (such as a double-blind study of a drug) that has no therapeutic effect on the condition being treated but may produce side effects (such as drowsiness or nausea) similar to those of the substance whose effectiveness is being tested.

As used herein, "purified" does not require absolute purity but is instead intended as a relative definition. For example, purification of a starting material or a natural material to at least one order of magnitude, preferably two or three orders of magnitude is expressly contemplated as falling within the definition of "purified."

As used herein, "Swiss Chard" refers to a plant of Chenopodiaceae Family, *Beta vulgaris* subsp. *Cicla*, also known as stem chard, spinach beet, seakale beet, silver beet, perpetual spinach, leaf beet.

As used herein, the term "treating" in its various grammatical forms refers to preventing, curing, reversing, attenuating, alleviating, minimizing, suppressing or halting the deleterious effects of a disease state, disease progression, disease causitive agent or other abnormal condition.

II. Compositions and Methods for Delivery of Magnesium

In one embodiment, the disclosure relates to compositions and methods for delivery of magnesium. In one embodiment, the disclosure relates to compositions and methods for increased absorption of magnesium. In another embodiment, the disclosure relates to compositions and methods for increasing magnesium in the cerebrospinal fluid of an individual. In one embodiment, the disclosure relates to compositions and methods for increased bioavailability of magnesium as compared to the salt form of Mg.

In one embodiment, the disclosure relates to a composition comprising a first plant based source of magnesium and a second plant based source of magnesium. In one embodiment, the first plant based source is a pseudograin.

In one embodiment, the disclosure relates to a composition comprising a first plant based source of magnesium and a second plant based source of magnesium, wherein the second plant based source of magnesium is a leafy vegetable.

In one embodiment, the disclosure relates to a composition comprising a first plant based source of magnesium and a second plant based source of magnesium, wherein the first plant based source is a pseudograin and the second plant based source of magnesium is a leafy vegetable.

In one embodiment, the disclosure relates to a composition comprising a first plant based source of magnesium and a second plant based source of magnesium, wherein the first plant based source is a pseudograin and the second plant based source of magnesium is a leafy vegetable, and the leafy vegetable is about 50% more on a dry weight basis as compared to the weight of the pseudograin.

In one embodiment, the disclosure relates to a composition comprising a pseudograin and a leafy vegetable, wherein the leafy vegetable and the pseudograin are present at a ratio of 3:2 on a dry weight basis.

In one embodiment, the disclosure relates to a composition comprising a first plant based source of magnesium and a second plant based source of magnesium, wherein the composition provides increased bioavailability of magnesium as compared to the salt form of Mg. In one embodiment, the composition provides three times greater bioavailability of Mg as compared to the salt form of Mg.

In one embodiment, the disclosure relates to a composition comprising a first plant based source of magnesium and a second plant based source of magnesium, wherein the composition provides free ionic Mg to the CNS of an individual without a side effect of constipation.

In one embodiment, the composition, which is preferably in the form of a powder, can be dispersed in foods or drinks so as to have a daily intake in magnesium as described above, which depends mainly on the desired effect and target tissue. The amount of the composition or food composition to be consumed by the individual to obtain a beneficial effect will also depend upon on the size and age of the individual.

In one embodiment, the nutritional supplement or dietary supplement or composition for oral administration may be in capsules, gelatin capsules, soft capsules, tablets, sugar-coated tablets, pills, pastes or pastilles, gums, or drinkable solutions or emulsions, a syrup or a gel, which can then be taken directly with water or by any other known means. This supplement may also include a sweetener, a stabilizer, an antioxidant, an additive, a flavoring or a colorant.

In one embodiment, the composition can have a dry weight of about 6.35 grams and mixed with about 8 ounces of fluid.

In one embodiment, the composition can have a dry weight from about 5 grams to about 10 grams and mixed with from about 8 ounces to about 12 ounces of fluid.

III. Pseudograin

In one embodiment, the composition comprises a pseudograin. In one embodiment, the composition comprises a powder, flour or extract from one or more pseudograins.

In one embodiment, the composition comprises one or more pseudograin as a first source of magnesium. In one embodiment, the composition comprises at least two sources of magnesium. In one embodiment, the pseudograin represents the first source of magnesium and is present in the composition at about 50% less by weight as compared to the second source of magnesium. In one embodiment, the pseudograin representing the first source of magnesium is present in the composition from about 40% to about 60% less by weight as compared to the second source of magnesium.

In one embodiment, the composition comprises a first source of magnesium and a second source of magnesium, wherein the first source is a pseudograin and the first and second source of magnesium are present in a 2:3 ratio, respectively, on a dry weight basis.

In one embodiment, the one or more pseudograin comprises about 35% by weight of the composition. In one embodiment, the one or more pseudograin comprises from about 20% to about 50% by weight of the composition on a dry weight basis. In still another embodiment, the one or more pseudograin comprises from about 25% to 45% by weight of the composition on a dry weight basis. In yet another embodiment, the one or more psuedograin comprise from 30% to about 40% by weight of the composition on a dry weight basis.

In one embodiment, the pseudograin includes but is not limited to Amaranth (Love-lies-bleeding, Red amaranth, Prince-of-Wales-feather); Breadnut; Buckwheat; Chia; Cockscomb; Pitseed Goosefoot; Qañiwa; *Quinoa*; teff; wild rice, and Wattleseed (also called acacia seed)

In one embodiment, the pseudograin is Buckwheat.
A. Buckwheat

Buckwheat is referred to in the literature as a pseudograin, because botanically buckwheat belongs to the Polygonaceae plants (knotweed family), although it is edible in a manner comparable to that of cereal grains. The name buckwheat originates from its wheat-like ingredients and its external appearance, which resembles that of beechnuts. From the standpoint of nutritional physiology, buckwheat is more valuable than conventional varieties of wheat, especially since buckwheat has a higher essential amino acid content and thus has a very high biological value. In addition, buckwheat is gluten-free, so it is also suitable for individuals having celiac disease, that is, sprue.

In one embodiment, the composition disclosed herein comprises ground Buckwheat or a Buckwheat powder or a Buckwheat flour or a Buckwheat extract formed from buckwheat. In one embodiment, the dietary supplement comprises ground Buckwheat or a Buckwheat powder or Buckwheat flour or a Buckwheat extract formed from buckwheat.

In one embodiment, the ground Buckwheat or Buckwheat powder or Buckwheat flour or Buckwheat extract is obtained from buckwheat kernels, whether in natural form or in pre-roasted form, also known as kascha, as hard kernels. In another embodiment, the Buckwheat can be obtained from buckwheat kernels that are subjected to a swelling process in combination with the addition of water.

In one embodiment, the Buckwheat flour is a whole buckwheat flour. In another embodiment, the Buckwheat flour is a light buckwheat flour.

In one embodiment, the Buckwheat flour is a combination of whole buckwheat flour and light buckwheat flour. The whole buckwheat flour component is a buckwheat flour made by milling the whole buckwheat including the hulls. Consequently, greater than 99% of such buckwheat flour passes through a 60-mesh U.S. standard screen and is slightly grey in appearance and imparts a grayish color in the final product. The light buckwheat flour component is a buckwheat flour made by milling buckwheat without the hulls, thereby producing a flour having a white appearance.

In one embodiment, the ground Buckwheat or Buckwheat powder is made from ground buckwheat hulls, made substantially only of buckwheat hulls.

In one embodiment, the Buckwheat is in the form of an extract.
B. Other Grains

In one embodiment, the composition can comprise one or more cereal grains. Examples of cereal grains include but are not limited to barley, corn, flax, sorghum, rice, maize, rye, spelt, triticale, millet, wheat, malted versions of these cereal grains and combinations of these grains. The cereal grains can be processed or unprocessed.

IV. Leafy Vegetable

In one embodiment, the composition further comprises one or more leafy vegetables. In one embodiment, the leafy vegetable is dried and ground into a powder.

In one embodiment, the one or more leafy vegetables comprise about 50% by weight of the composition on a dry weight basis. In one embodiment, the one or more leafy vegetables comprises from about 35% to about 65% by weight of the composition on a dry weight basis. In still another embodiment, the one or more leafy vegetables comprises from about 40% to 60% by weight of the composition. In yet another embodiment, the one or more leafy vegetables comprises from 45% to about 55% by weight of the composition on a dry weight basis.

In one embodiment, the composition comprises one or more leafy vegetables as a second source of magnesium. In one embodiment, the leafy vegetable represents the second source of magnesium and is present in the composition at about 50% more by weight as compared to the first source of magnesium. In one embodiment, the leafy vegetable representing the second source of magnesium is present in the composition at about 40% to about 60% more by weight as compared to the first source of magnesium. In one embodiment, the composition comprises a first source of magnesium and a second source of magnesium, wherein the second source is a leafy vegetable and the first and second source of magnesium are present in a 2 (first source):3 (second source, leafy vegetable) ratio by weight.

In one embodiment, the composition comprises one or more pseudograin as a first source of magnesium and one or more leafy vegetables as a second source of magnesium. In one embodiment, the composition comprises a pseudograin as a first source of magnesium and a leafy vegetable as a second source of magnesium, wherein the first and second source of magnesium are present in a 2:3 ratio by weight.

In one embodiment, the leafy vegetable or plant materials may be used in the form of fresh, concentrated or dried materials, for example, air or freeze dried material.

In one embodiment, the leafy vegetable includes but is not limited to chard, sugar beet, beetroot, kale, collard greens, turnip greens, mustard greens, spinach, beet greens, broccoli rabe, dandelion greens, water cress or gai lan, also known as Chinese broccoli.

A. Swiss Chard

In one embodiment, the leafy vegetable is Swiss Chard. Swiss chard (*Beta vulgaris*) is a leafy vegetable belonging to the family Amaranthaceae. All cultivated *Beta vulgaris* varieties fall into the subspecies *Beta vulgaris* subsp. vulgaris. The wild ancestor of these cultivated varieties is *Beta vulgaris* subsp. *maritima*, commonly known as the sea beet, and is found throughout the Mediterranean, the Atlantic coast of Europe, the Near East, and India. *Beta vulgaris* has four different cultivated forms: the common garden beet, also called beetroot or table beet, is a vegetable grown for its roots; the sugar beet is used to produce sugar; mangelwurzel is a fodder crop; and Swiss Chard, also known as chard, leaf beet or silverbeet, is grown for its nutrient-rich leaves. Though nowadays the generally accepted name for Swiss Chard is *Beta vulgaris* subsp. vulgaris, its taxanomic rank has changed many times, and Swiss Chard is also occasionally indicated as *Beta vulgaris* var. vulgaris or *Beta vulgaris* var. *cicla*.

Swiss Chard leaves are an excellent source of vitamins such as A, C, and K, and a good source of minerals such as iron, magnesium and potassium. Depending on the variety, the leaf blade may be green, dark green or reddish in color, while the petiole (also called the leaf stalk) and major veins (midrib and secondary veins) of the leaf may be white, green, yellow, orange, red or even purple. The yellow to reddish-purple colors are caused by the presence of different betalain pigments. There are two classes of betalains: (a) betacyanins that include the reddish to violet betalain pigments and (b) betaxanthins that include the yellow to orange betalain pigments.

TABLE II

| Representative varieties of Swiss Chard | | |
|---|---|---|
| Burpee's Rhubarb Chard Swiss Chard | Large White Ribbed Swiss Chard | Rhubarb Supreme Swiss Chard |
| Verte a Carde Blanche Swiss Chard | Magenta Sunset Swiss Chard | Golden Swiss Chard |
| Verde da Taglio Swiss Chard | Mangold Witerbi Swiss Chard | Pink Swiss Chard |
| Fordhook Glant Swiss Chard | Orange Fantasia Swiss Chard | Canary Yellow Swiss Chard |
| Bright Lights Swiss Chard | Orea Swiss Chard | Flamingo Pink Swiss Chard |
| Five Color Sliverbeet Swiss Chard | Pink Passion Swiss Chard | Oriole Orange Swiss Chard |
| Verde a costa blanca- Swiss Chard | Rainbow Swiss Chard | Vulcan Swiss Chard |
| Lucullus Swiss Chard | Silverado Swiss Chard | Pink Lipstick Swiss Chard |
| Monstruoso Swiss Chard | White King Swiss Chard | Umaina Swiss Chard |
| Perpetual Spinach Swiss Chard | Erbette Swiss Chard | Bietola da Coste Bionda de Lione Swiss Chard |
| Rhubarb Swiss Chard | Virgo Swiss Chard | Barese Swiss Chard |
| Argentata Swiss Chard | Italian Silver Rib Swiss Chard | Cardinal Swiss Chard |
| Bright Yellow Swiss Chard | Scarlet Chariotte Swiss Chard | Glatter Silber Swiss Chard |
| Burpee's Fordhook Glant Swiss Chard | Golden Sunrise Swiss Chard | Feurio Swiss Chard |

TABLE II-continued

| Representative varieties of Swiss Chard | | |
|---|---|---|
| Charlotte Swiss Chard | Broadstem Green Swiss Chard | Sea Foam Swiss Chard |
| French Swiss Chard | Bionda di Lyon Swiss Chard | Gold Glebe Swiss Chard |
| Discovery Swiss Chard | Peppermint Swiss Chard | |

In one embodiment, the Swiss Chard is in the form of an extract. In another embodiment, the Swiss Chard is in the form of a powder. In still another embodiment, the Swiss Chard is in the form of a lyophilized extract.

V. Monk Fruit

Monk fruit is a small, green gourd that resembles a melon. Monk fruit is grown in Southeast Asia. Monk fruit is usually dried and used to make medicinal teas. Monk fruit sweeteners are made from the fruit's extract.

In one embodiment, the composition further comprises a monk fruit extract. Monk fruit extract containing mogroside V can be one component of the compositions/dietary supplements described herein.

Methods of obtaining such monk fruit extracts (sometimes referred to as Luo Han Guo extracts) are well known in the art and any of such methods may be utilized in order to prepare the monk fruit extract to be employed in the present compositions. Suitable preparation methods are described, for example, in U.S. Patent Publication 2011/0021456. Prior to use in the compositions described herein, the monk fruit extract may be subjected to various purification procedures in order to reduce or eliminate off-flavors, off-colors and/or off-tastes that might otherwise be present. Examples of such purification procedures include, without limitation, treatment with activated carbon, treatment with various types of ion exchange resins or other adsorbents, and the like. Typically, the monk fruit extract is in dry, powdered form. but in alternative embodiments the monk fruit extract may be in solution form (e.g., as a concentrated aqueous solution or syrup).

In one embodiment, a monk fruit extract having a relatively high mogroside V content, e.g., at least 20, at least 25. at least 30, at least 35. at least 40 or at least 45 weight % mogroside V (on a dry solids basis) can be used. The monk fruit extract may be essentially pure (i.e., at least 95 weight % pure) mogroside V.

In one embodiment, the monk fruit extract may contain less than 95, less than 90, less than 85, less than 80, less than 75, less than 70 or less than 65 weight % mogroside V (on a dry solids basis). For example, the monk fruit extract may have a mogroside V content of 45 to 55 weight %. In addition to the mogroside V, the monk fruit extract may contain other constituents, in particular other terpene glycosides such as mogroside II-IV and VI, II-oxo-mogroside V, grosmomoside I, and siamenoside I as well as protein fragments, melanoidins and flavonoids Monk fruit extracts available from commercial sources may be used. For example, the monk fruit extracts sold under the brand names PUREFRUIT (by Tate & Lyle) and FRUIT-SWEETN ESS (by BioVittoria) are generally suitable for use.

In one embodiment, the monk fruit extract is about 1.5% by weight on a dry weight basis of the composition. In one embodiment, the berry concentrate is from about 0.5% to about 5% by weight on a dry weigh basis of the composition.

VI. Berry Concentrate

In one embodiment, the composition further comprises a berry concentrate. In one embodiment, the concentrate is in the form of a powder. In one embodiment, the berry concentrate is a mixed berry concentrate. In yet another embodiment, the mixed berry concentrate is organic.

In one embodiment, the berry concentrate comprises one or more of the following fruits and/or fruit flavors: apple, banana, blueberry, cantaloupe, cranberry, kiwi, lime, lemon, mango, melon, nectarine, orange, *papaya*, peach, pear, pineapple, plum, raspberry, strawberry, In one embodiment, the berry concentrate is about 3% by weight on a dry weight basis of the composition. In one embodiment, the berry concentrate is from about 1% to about 10% by weight on a dry weigh basis of the composition.

VII. Nu-Flow

In one embodiment, the composition further comprises a biogenic silica from a plant material. In one embodiment, the biogenic silica is from a plant material such as rice hulls, rice straw and so forth containing a significant amount of silica for use as an anti-caking agent, excipient or flavor carrier. When the plant material is certified as organic, the silica may also be certified as organic.

The plant material is ground and the silica may be concentrated by carbon reduction through enzymatic treatment or burning. In some instances an antimicrobial treatment of the silica may be beneficial.

In one embodiment, the biogenic silica is Nu-FLOW. Nu-FLOW is made from rice hulls that are sterilized and ground to a fine powder. Nu-FLOW is a natural alternative to silicon dioxide or other anti-caking/flow agents and it can be used to improve processing flows.

In one embodiment, Nu-Flow is about 15% by weight on a dry weight basis of the composition. In one embodiment, the Nu-Flow is from about 5% to about 20% by weight on a dry weigh basis of the composition.

VIII. Formulations for Oral Administration

Oral dosage forms may be as a solid, gel or liquid. Examples of solid dosage forms include, but are not limited to pillules, tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the disclosure are provided as solid dosage forms, preferably capsules, tablets or powders. The tablets, pillules, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, lycopodium and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compositions and formulations according to the disclosure may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

Compositions and formulations may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present disclosure include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410, 545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. 4,358,603.

The disclosure is now described with reference to the following Examples. These Examples are provided for the purpose of illustration only and the invention should in no way be construed as being limited to these Examples, but rather should be construed to encompass any and all variations that become evident as a result of the teaching provided herein.

IX. Methods for Delivery of Magnesium

In one embodiment, the disclosure relates to methods for the delivery of magnesium to an individual. In one embodiment, the disclosure relates to methods for the delivery of magnesium to an individual comprising administering a composition as disclosed herein in an effective amount to an individual. In one embodiment, the disclosure relates to methods for increasing bioavailability of Mg in the CNS of an individual comprising administering one or more compositions disclosed herein.

In one embodiment, the disclosure relates to methods for increasing magnesium in the cerebrospinal fluid of an individual comprising administering a composition as disclosed herein in an effective amount to the individual.

In one embodiment, the disclosure relates to a method for delivery of magnesium to the central nervous system comprising: administering to an individual having a baseline level of free ionic magnesium in the central nervous system an effective amount of a composition having a pseudograin as a first plant based source of magnesium and a leafy vegetable as a second plant based source of magnesium, and increasing free ionic magnesium in the central nervous system of the individual as compared to the baseline. In one embodiment, the baseline level is the initial level or starting point.

In another embodiment, the disclosure relates to a method for delivery of magnesium to the central nervous system comprising: administering to an individual an effective amount of a composition having a pseudograin as a first plant based source of magnesium and a leafy vegetable as a second plant based source of magnesium, and increasing free ionic magnesium in the central nervous system of the individual as compared to a second individual not receiving the composition. In one embodiment, free ionic magnesium is increased as compared to an average level based on a population. In another embodiment, free ionic magnesium is increased as compared to reported levels in the scientific literature.

In another embodiment, the disclosure relates to a method for delivery of magnesium comprising: administering to an individual an effective amount of a composition having a pseudograin as a first plant based source of magnesium and a leafy vegetable as a second plant based source of magnesium, and increasing cognitive function of the individual as compared to a second individual not receiving the composition or as compared to a baseline cognitive function of the individual.

In another embodiment, the disclosure relates to a method for delivery of magnesium comprising: administering to an individual an effective amount of a composition having a pseudograin as a first plant based source of magnesium and a leafy vegetable as a second plant based source of magnesium, and increasing long and/or short term memory of the individual as compared to a second individual not receiving the composition or as compared to a baseline long and/or short term memory of the individual.

In another embodiment, the disclosure relates to a method for delivery of magnesium comprising: administering to an individual an effective amount of a composition having a pseudograin as a first plant based source of magnesium and a leafy vegetable as a second plant based source of magnesium, and reducing anxiety of the individual as compared to a second individual not receiving the composition or as compared to a baseline anxiety level of the individual.

In another embodiment, the disclosure relates to a method for delivery of magnesium comprising: administering to an individual an effective amount of a composition having a pseudograin as a first plant based source of magnesium and a leafy vegetable as a second plant based source of magnesium, and reducing incidence of a migraine headache of the individual as compared to a second individual not receiving the composition or as compared to a baseline migraine incidence of the individual.

In one embodiment, administration of the composition having a pseudograin as a first plant based source of magnesium and a leafy vegetable as a second plant based source of magnesium can reduce insulin resistance, reduce chronic inflammation, lower blood pressure, help control blood sugar levels, help control A1c levels, improve mood, improve exercise performance, reduce incidence of depression, and improve nervous system regulation as compared to a second individual not receiving the composition or compared to a baseline level of the individual.

In one embodiment, the composition is as recited in Table III below.

In one embodiment, the composition is delivered by mixing with a fluid and having the individual ingest the fluid.

In one embodiment, the composition is delivered by mixing with a food and having the individual ingest the food. In one embodiment, the food is a dairy product.

Example 1

A composition as recited in Table III was prepared. Dry weight of the composition was 6.35 g.

The composition is a plant based, multi-form source of magnesium, which is made from Swiss Chard (beet leaf) and buckwheat grown on sustainable and certified organic farms. The composition is designed to till nutritional gaps, in a natural way.

TABLE III

| Plant-based, multi-form source of Magnesium Composition | | |
|---|---|---|
| Raw Material | Units per Serving | Units |
| MIXED BERRY OC | 0.20 | grams |
| MONK FRUIT CONCENTRATE | 0.10 | grams |
| SWISS CHARD EXTRACT DRYER - ORGANIC | 3.10 | grams |
| BUCKWHEAT EXTRACT - ORGANIC | 2.15 | grams |
| NU-FLOW - ORGANIC | 0.80 | grams |

The composition can be dissolved into a liquid, or mixed with food, including yogurt, smoothies, shakes, protein shakes, or as a powder sprinkled over food. The composition can be dissolved in a fluid, including but not limited to water.

Example 2

Objective

We tested the effect of a composition comprising two plant based sources of magnesium, with buckwheat being one source of magnesium and Swiss Chard being a second source of magnesium versus other Mg forms on increasing free $Mg^{2+}$ levels in CSF of rats on Mg-deficient diet. The composition comprising two plant based sources of magnesium, with buckwheat being one source of magnesium and Swiss Chard being a second source of magnesium is referred to as EZ-Mg in this study. The composition has about 3 grams of swiss chard extract per serving and about 2 grams of buckwheat extract. The components of the EZ-Mg formulation are described in Table III.

Material and Methods

A. Animals

Male Sprague Dawley rats (150-175 grams on arrival) from Envigo (Indianapolis, IN) were used in the study. Upon receipt, rats were assigned unique identification numbers and were group housed with 2-3 rats per cage in polycarbonate cages with micro-isolator filter tops. All rats were examined and weighed prior to initiation of the study to assure adequate health and suitability. During the course of the study, 12/12 light/dark cycles will be maintained. The room temperature will be maintained between 20° C. and 23° C. with a relative humidity maintained around 50%.

Upon start of the study, animals (except for the normal Mg diet group, N=15) were placed on a diet of LabDiet 5008, which contains 0.2% Mg. Chow (LabDiet 5008), diet deficient in Mg, and water were provided ad libitum for the duration of the study.

B. Treatment Groups

Oral treatment 20 mg/kg twice a day (40 mg/kg total per day) at dose volume of 5 mL/kg. N=15 per group.

1. Low Mg chow (0.2% Mg)—Placebo
2. Low Mg chow (0.2% Mg)—SPMg formula E-Z Mg (1.5% Mg)
3. Low Mg chow (0.2% Mg)—Mg threonate (Magtein 7.7% Mg)
4. Low Mg chow (0.2% Mg)—Mg citrate (11.5% Mg)
5. Low Mg chow (0.2% Mg)—Mg bisglycinate (11.7% Mg)
6. Normal chow (0.23% Mg)—no treatment C. Collections 1. Baseline Collections Rats were anaesthetized with isoflurane and placed in a stereotaxic frame. The atlanto-occipital membrane was exposed and a microneedle was inserted into the cisterna *magna* via the atlanto-occipital membrane. Approximately 25-50 µL of CSF was slowly extracted. A small piece of moist collagen foam was used to seal the punctured membrane. The exposed muscle and skin was sutured in layers and the animal placed in a warmed chamber to recover from anaesthesia before returning to the home cage. Animals received 5 mg/kg carprofen sub-cutaneously as post-operative analgesic and again at 24 hrs.

2. Terminal Collections

On the morning of the 15th day (i.e. the day after the completion of 14 days of treatment) animals were anaesthetized with Pentobarbital (60 mg/kg) prior to terminal CSF collections. The atlanto-occipital membrane is exposed and ~0.1 mL of CSF was slowly extracted from the cisterna *magna* and frozen on dry ice.

Statistical Analysis

Data was analyzed by analysis of variance (ANOVA) followed by post-hoc comparisons where appropriate. For analysis with missing data, a mixed-model ANOVA was used. An effect will be considered significant if $p<0.05$. Data is presented as the mean and standard error to the mean (s.e.m).

Results

A. Body Weight

Figure 1:
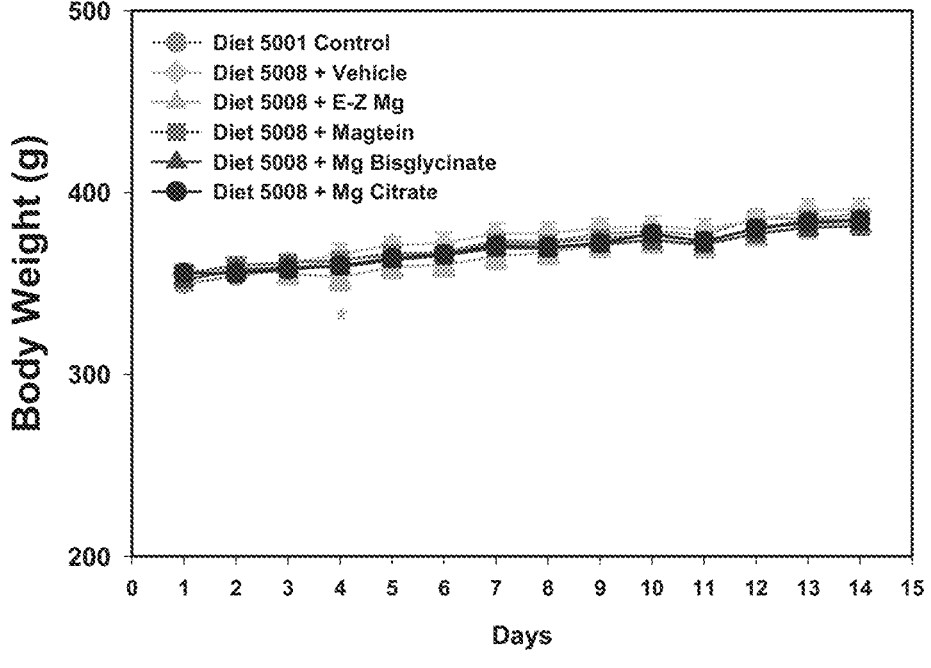
FIG. 1 is a line graph depicting body weights of animals during a magnesium study. The *$p < 0.05$ is compared to Diet 5001 Control. Data are presented as mean±SEM.

Body weights of rats are shown in FIG. 1. Repeated measures ANOVA showed no overall difference between groups but a significant interaction between group and time. Post hoc analysis indicated that animals fed with Diet 5008 and treated with E-Z Mg had a lower body weight than vehicle-treated animals at Day 4 of the study. There were no other statistically significant differences between any groups at any of the other time points.

B. Magnesium in CSF

Figure 2:
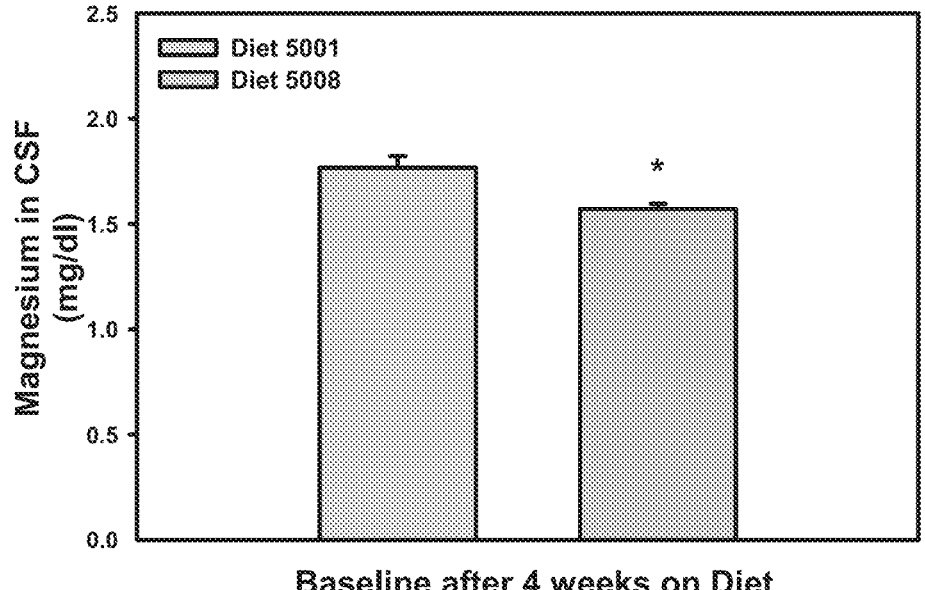
FIG. 2 is a bar graph depicting baseline magnesium levels in CSF of animals following 4 weeks on Diet 5001 (0.23%

Magnesium levels in the CSF of animals after 4 weeks on Diet 5001 (0.23% Mg) and Diet 5008 (0.20% Mg) are shown in FIG. 2. Animals that were fed Diet 5008 showed a significant decrease in CSF Mg levels compared to animals that were fed Diet 5001.

CSF magnesium levels following 14 days of supplementary magnesium treatment are shown in FIG. 3. The percent change in the average level of magnesium in the CSF is shown in FIG. 4. A mixed model repeated measures ANOVA showed a strong overall trend towards differences between treatment groups (p=0.0728). Posthoc analysis showed that animals treated with a composition comprising two plant based sources of magnesium, with buckwheat being one source of magnesium and Swiss Chard being a second source of magnesium, showed a strong increase in CSF magnesium at Day 15 compared to baseline measurements (p=0.066). Also at Day 15, animals treated with the composition comprising two plant based sources of magnesium, with buckwheat being one source of magnesium and Swiss Chard being a second source of magnesium showed strong trends towards high CSF magnesium compared to Diet 5008+Vehicle animals (p=0.063).

Summary

This study showed that 4 weeks of magnesium deficient Diet 5008 (0.20% Mg) significantly reduced magnesium levels in the cerebrospinal fluid (CSF) compared to feeding on Diet 5001 (0.23% Mg). Treatment with E-Z Mg (1.5%

Mg) at 20 mg/kg twice a day (40 mg/kg total per day) at a dose volume of 5 mL/kg for 14 days showed a strong trend to increasing CSF Mg levels.

Example 3

Objective

The goad of the study was to evaluate the efficacy of a composition (EZ-Mg) having two plant based sources of magnesium, with buckwheat being one source of magnesium and Swiss Chard being a second source of magnesium on free $Mg^{2+}$ levels in CSF. The formulation of EZ-Mg is described in Table III.

Material and Methods

A. Animals

Male Sprague Dawley rats (150-175 grams on arrival) from Envigo (Indianapolis, IN) were used in the study. Upon receipt, rats were assigned unique identification numbers and were group housed with 2-3 rats per cage in ventilated cages with micro-isolator filter tops. All rats were examined and weighed prior to initiation of the study to assure adequate health and suitability. During the course of the study, 12/12 light/dark cycles will be maintained. The room temperature will be maintained between 20° C. and 23° C. with a relative humidity maintained around 50%.

On the day of arrival to the research facility, animals (except for the normal Mg diet group, N=15) were placed on LabDiet 5008, a diet that is deficient in Mg containing 0.20% magnesium. Another group (control) of rats (N=15) were placed on a normal diet (LabDiet 5K67, containing 0.23% of magnesium) for the duration of the study and served as controls.

B. Treatment Groups

1. Normal chow—Water;
2. Low Mg chow—Water;
3. Low Mg chow—E-Z Mg (1.5% Mg);
4. Low Mg chow—Mg threonate (Magtein 7.7% Mg); and
5. Low Mg chow—Mg citrate (11.5% Mg)

Results

A. Body Weight

Body weights of the rats are shown in FIG. 5. Two-way ANOVA showed significant main effect of Day ($F_{(4,2024)}$ =780.991, P<0.001), insignificant main effect of Treatment ($F_{(4,2024)}$=1.729, P>0.05), and no significant Day×Treatment interaction ($F_{(4,2024)}$=0.118, P>0.05). The main effect of Day clearly indicates the steady body weight gain of the rats.

B. CSF

Prior to the start of Mg dosing on Day 1, rats were anaesthetized with isoflurane and placed in a stereotaxic frame. The atlanto-occipital membrane was exposed and a microneedle was inserted into the cisterna *magna* via the atlanto-occipital membrane. Approximately 25-50 µL of CSF was slowly extracted. A small piece of moist collagen foam was used to seal the punctured membrane. The exposed muscle and skin was sutured in layers and the animal placed in a warmed chamber to recover from anesthesia before returning to the home cage. Animals received 5 mg/kg carprofen sub-cutaneously as post-operative analgesic and again at 24 hrs.

CSF was again collected at Day 15 for interim analysis. On the morning of the 45th day (i.e. the day after the completion of 44 days of treatment) animals were anaesthetized prior to terminal CSF collections. The atlanto-occipital membrane was exposed and about 0.1 mL of CSF was slowly extracted from the cisterna *magna* and frozen on dry ice. Samples were shipped to Pronexus for analysis.

Data of Mg levels in CSF were analyzed by using one-way ANOVA followed by Fisher's LSD post hoc test on baseline, Day 15 and Day 45 separately, with significance set at $P<0.05$. Animals whose data fell above or below two standard deviations from the mean at any data points were removed as outliers from the data analysis.

As shown in FIG. 6, EZ Mg replenishes free ionic Mg (the physiologically functional Mg) in the Central Nervous System. Both EZ Mg and Magtein showed better delivery of Mg to the CNS in comparison to Mg citrate and magnesium bisglycinate, however, EZ-Mg provided the best results.

C. Novel Object Recognition

The Novel Object Recognition (NOR) is a test of recognition learning and memory retrieval, which takes advantage of the spontaneous preference of rodents to investigate a novel object compared to a familiar one. NOR test was conducted in an open-field arena (40×40 cm) placed in a sound-attenuated room under dimmed lighting. Each rat was tested separately. All training and testing trials were videotaped and scored by an observer blind to treatments.

On days 1 and 2, rats were allowed to freely explore the arena (no objects inside) for a 5-minute habituation period. On Day 3 (training and testing day), rats ware placed into the test arena in the presence of two identical objects (Object A-A or Object B-B) for 3 min. One hour later, the rats were again placed into the test arena in the presence of one familiar object and one novel object (Object A and Object B), and the time spent exploring both objects is recorded. The presentation order and position of the objects (left/right) was randomized between rats to prevent bias from order or place preference.

Data of NOR test (T2) were expressed as Recognition Index, which is defined as the ratio of the time spent exploring the novel object over the total time spent exploring both objects (Novel/(Familiar+Novel)×100%) during the test session. Data were analyzed by using one-way ANOVA followed by Fisher's LSD post hoc test (and t-test when necessary) on 0-3 minute time range of T2, with significance set at $P<0.05$. Rats with recognition index above 90% or below 30% during the first minute of T2 were eliminated because they suggest strong (non-memory) bias between two objects. Also the animals whose data fell above or below two standard deviations from the mean are removed as outliers from the final analysis.

As shown in FIG. 7, EZ-Mg supplementation showed significant improvement in cognitive function (Novel Object Recognition test) in comparison to Magtein and placebo control. Rats fed low Mg diet but supplemented with EZ Mg showed improved learning and memory in comparison to rats fed low diet and supplemented with Magtein or placebo. Mg citrate supplementation showed a trend toward improvement in cognitive function likely due to citric acid in the formula.

The disclosure will now be further described in the following paragraphs:

1. A composition comprising a first plant based source of magnesium and a second plant based source of magnesium, wherein the first plant based source is a pseudograin.

2. A composition comprising a first plant based source of magnesium and a second plant based source of magnesium, wherein the second plant based source of magnesium is a leafy vegetable.

3. A composition comprising a first plant based source of magnesium and a second plant based source of magnesium, wherein the first plant based source is a pseudograin and the second plant based source of magnesium is a leafy vegetable.

4. A composition comprising a first plant based source of magnesium and a second plant based source of magnesium, wherein the first plant based source is a pseudograin and the second plant based source of magnesium is a leafy vegetable, and the leafy vegetable is about 50% more on a dry weight basis as compared to the weight of the pseudograin.

5. A composition comprising a pseudograin and a leafy vegetable, wherein the leafy vegetable is about 50% more on a dry weight basis as compared to the weight of the pseudograin.

6. A composition comprising a first plant based source of magnesium and a second plant based source of magnesium, wherein the first plant based source is Buckwheat and the second plant based source of magnesium is Swiss Chard.

7. A composition comprising Buckwheat and Swiss Chard, wherein the Swiss Chard is about 50% more on a dry weight basis as compared to the weight of the Buckwheat.

8. A dietary supplement comprising a powder of Buckwheat and Swiss Chard, wherein the Swiss Chard is about 50% more on a dry weight basis as compared to the weight of the Buckwheat.

9. A composition comprising Buckwheat and Swiss Chard, wherein the Swiss Chard and Buckwheat are present at a ratio of 3:2 on a dry weight basis.

10. A dietary supplement comprising a powder of Buckwheat and Swiss Chard, wherein the Swiss Chard and Buckwheat are present at a ratio of 3:2 on a dry weight basis.

11. A composition comprising a pseudograin and a leafy vegetable, wherein the leafy vegetable and the pseudograin are present at a ratio of 3:2 on a dry weight basis.

12. A composition of any of the preceding paragraphs further comprising a monk fruit extract.

13. A composition of any of the preceding paragraphs further comprising a berry concentrate.

14. A composition of any of the preceding paragraphs further comprising a biogenic silica from a plant material.

15. A composition of any of the preceding paragraphs, wherein the composition is in the form of a powder.

16. A composition of any of the preceding paragraphs, wherein the composition is in the form a pill or tablet.

17. A composition of any of the preceding paragraphs, wherein the pseudograin is Buckwheat.

18. A composition of any of the preceding paragraphs, wherein the leafy vegetable is Swiss Chard.

19. A composition of any of the preceding paragraphs, wherein the pseudograin is Amaranth or Breadnut or Buckwheat or Chia or Cockscomb or Pitseed Goosefoot or Qañiwa or *Quinoa* or teff or wild rice; or Wattleseed.

20. A composition of any of the preceding paragraphs, wherein the leafy vegetable is chard or sugar beet or beetroot or kale or collard greens or turnip greens or mustard greens or spinach or beet greens or broccoli rabe or dandelion greens or water cress or gai lan.

21. A method for increasing the concentration of magnesium in the cerebrospinal fluid of an individual comprising administering to an individual an effective amount of a dietary supplement or composition of any of the preceding claims.

22. A method for delivering magnesium comprising administering to an individual an effective amount of a dietary supplement or composition of any of the preceding claims.

What is claimed is:

1. A dietary supplement consisting of: a composition of a buckwheat, a swiss chard, a binder, and a vegetable oil, wherein the swiss chard and the buckwheat are at a ratio of 3:2 on a dry rate basis, and further wherein the composition provides increased bioavailability of magnesium as compared to a salt form of Mg.

2. A dietary supplement consisting of: a composition of a buckwheat powder, a swiss chard powder, a binder, rice hulls and a vegetable oil, wherein the buckwheat powder provides a first plant based source of magnesium and the swiss chard powder provides a second plant based source of magnesium, wherein the buckwheat powder is from 30% to 40% on a dry weight basis of the composition, and the swiss chard powder is from 45% to 55% on a dry weight basis of the composition.

3. A dietary supplement consisting of: a composition of a buckwheat powder, a swiss chard powder, a binder, rice hulls and a vegetable oil, wherein the buckwheat powder provides a first plant based source of magnesium and the swiss chard powder provides a second plant based source of magnesium, wherein the swiss chard powder and the buckwheat powder are in a 3:2 ratio on a dry weight basis, and further wherein the composition provides increased bioavailability of magnesium as compared to a salt form of Mg.

\* \* \* \* \*